United States Patent [19]
Willmann et al.

[11] Patent Number: 5,993,767
[45] Date of Patent: Nov. 30, 1999

[54] SOLVATE OF LITHIUM HEXAFLUOROPHOSPHATE AND PYRIDINE, ITS PREPARATION AND PREPARATION PROCESS FOR LITHIUM HEXAFLUOROPHOSPHATE USING SAID SOLVATE

[75] Inventors: Patrick Willmann, Montgiscard; Régine Naejus, Tours; Robert Coudert, Notre Dame D'Oe; Daniel Lemordant, Orsay, all of France

[73] Assignee: Centre National D'Etudes Spatiales, France

[21] Appl. No.: 09/000,232

[22] PCT Filed: Jun. 18, 1997

[86] PCT No.: PCT/FR97/01097

§ 371 Date: Jan. 23, 1998

§ 102(e) Date: Jan. 23, 1998

[87] PCT Pub. No.: WO97/48709

PCT Pub. Date: Dec. 24, 1997

[30] Foreign Application Priority Data

Jun. 19, 1996 [FR] France ................... 96 07623

[51] Int. Cl.⁶ ............ C01B 25/10; C07D 213/20; C07F 9/28
[52] U.S. Cl. ............ 423/301; 546/22; 546/347
[58] Field of Search ............. 423/301; 546/22, 546/347

[56] References Cited

U.S. PATENT DOCUMENTS 3,654,330  4/1972  Wiesboeck .
4,996,320  2/1991  Omemoto et al. ............ 546/22
5,378,445  1/1995  Salmon et al. ............ 423/301
5,616,636  4/1997  Avar et al. ............ 546/22

FOREIGN PATENT DOCUMENTS 20 26 110  12/1970  Germany .

OTHER PUBLICATIONS

Chemical Abstracts, vol. 100, No. 21, 21 Mai 1984, Columbus, Ohio, US; abstract no 174608c, Mohamed, K. er at.: "pyridinium poly (hydrogen fluoride)—a reagent for the preparation of hexafluorophosphates" XP002024671.

*Primary Examiner*—Wayne Langel
*Attorney, Agent, or Firm*—Burns, Doane, Swecker & Mathis, L.L.P.

[57] ABSTRACT

The invention relates to a lithium hexafluorophosphate solvate usable for the preparation of high purity lithium hexafluorophosphate.

This solvate of lithium hexafluorophosphate and pyridine complies with the formula:

$$Li(C_5H_5N)PF_6$$

and is prepared by a process comprising the following stages:

a) preparation of pyridinium hexafluorophosphate of formula $C_5H_5NHPF_6$ by the neutralization of hexafluorophosphoric acid $HPF_6$ with pyridine and b) conversion of the pyridinium hexafluorophosphate into solvate $LiPF_6$, $C_5H_5N$ by exchange with a lithium compound chosen from among lithium hydroxide, lithium alkoxides and alkyl-lithiums.

The $LiPF_6$ can be regenerated from the solvate by vacuum decomposition.

14 Claims, 7 Drawing Sheets

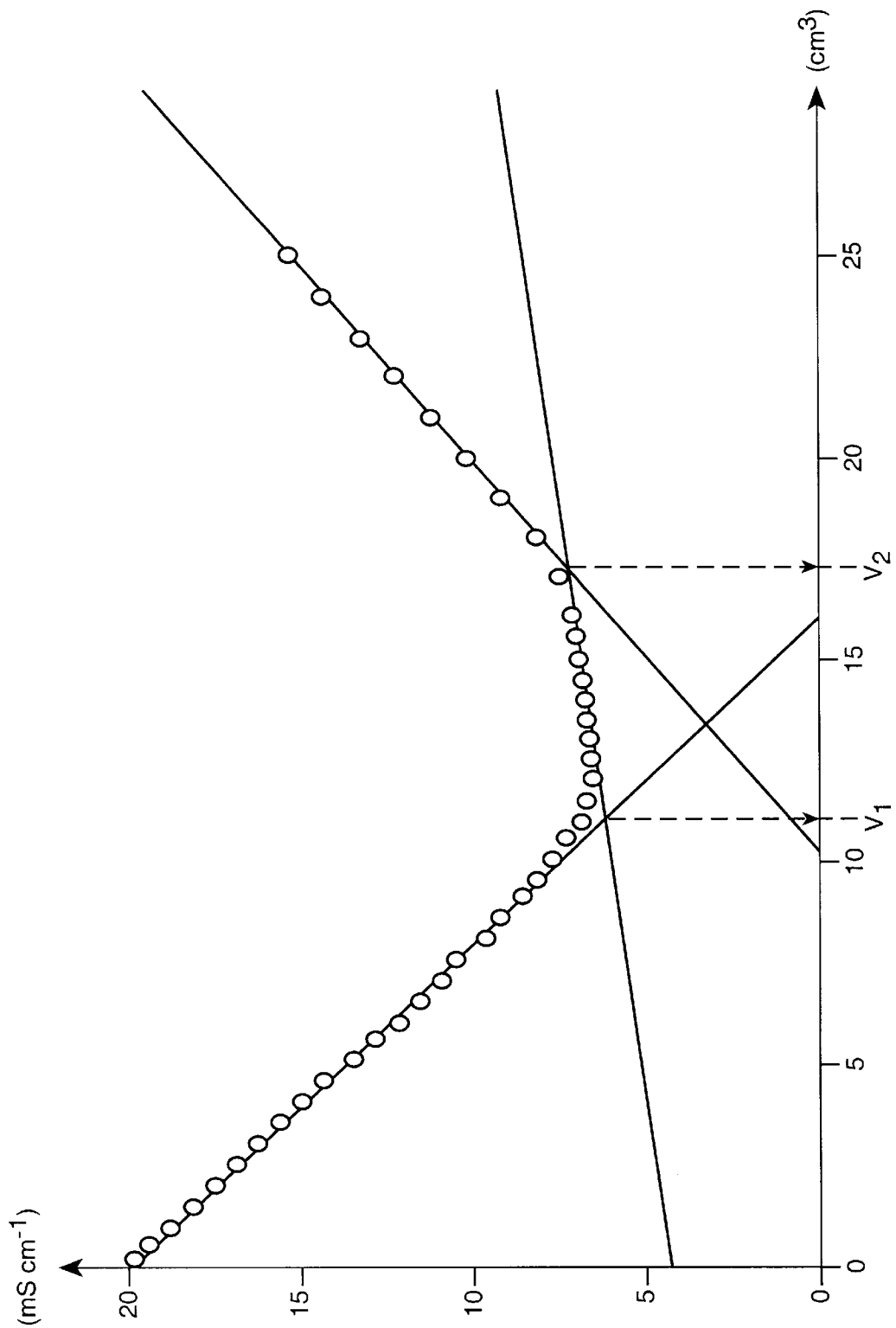
FIG._1

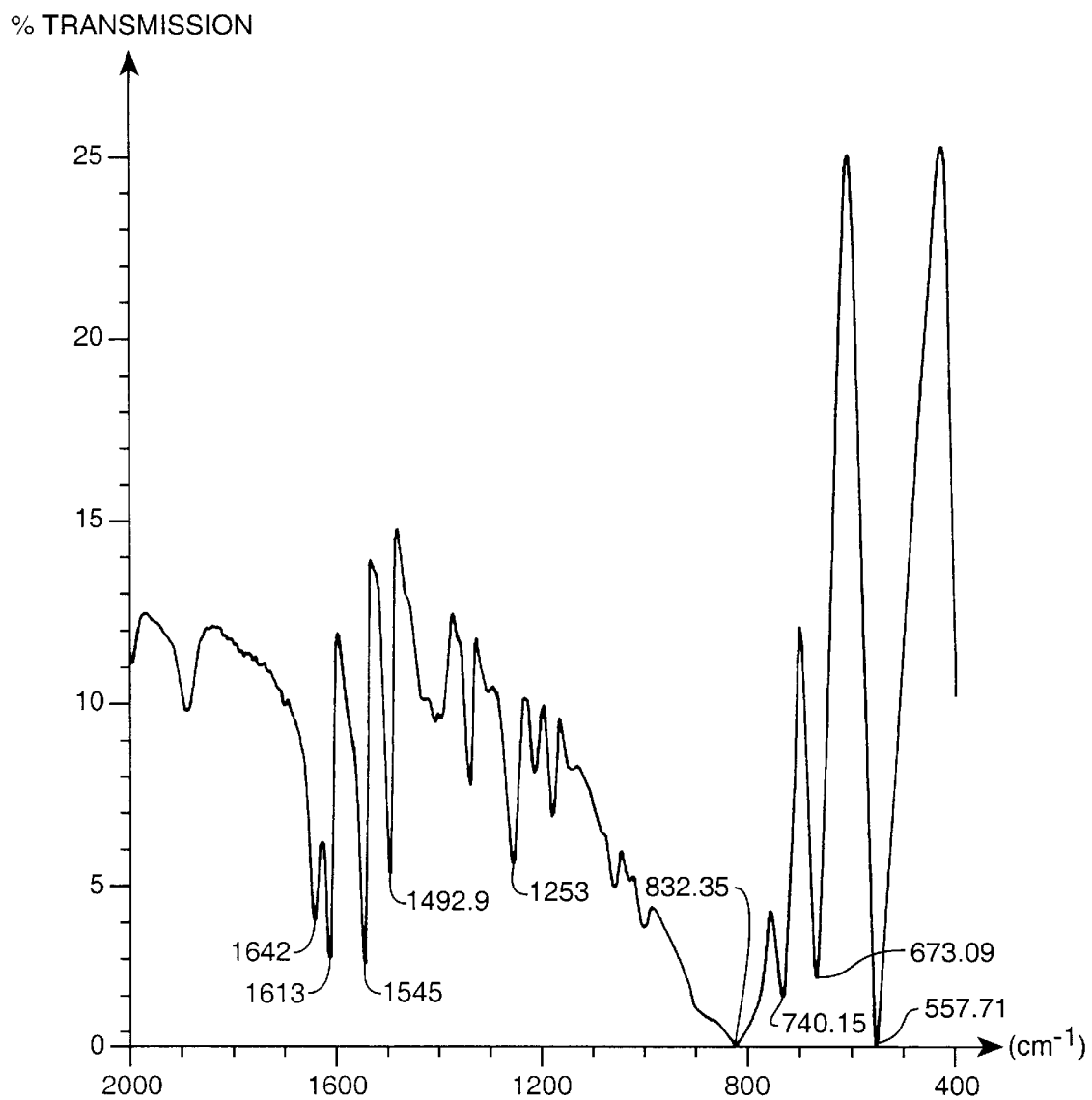
FIG._2

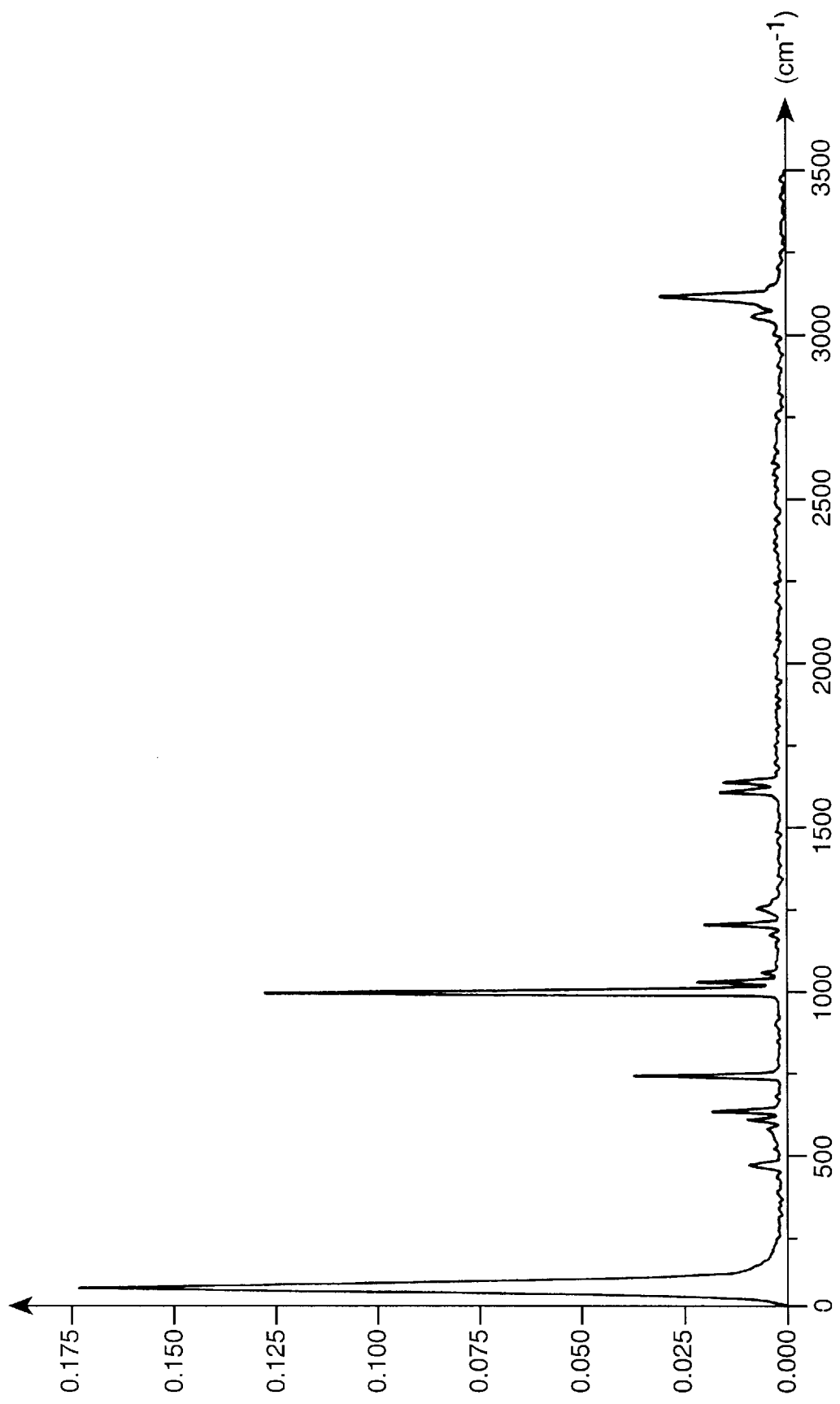
FIG._3

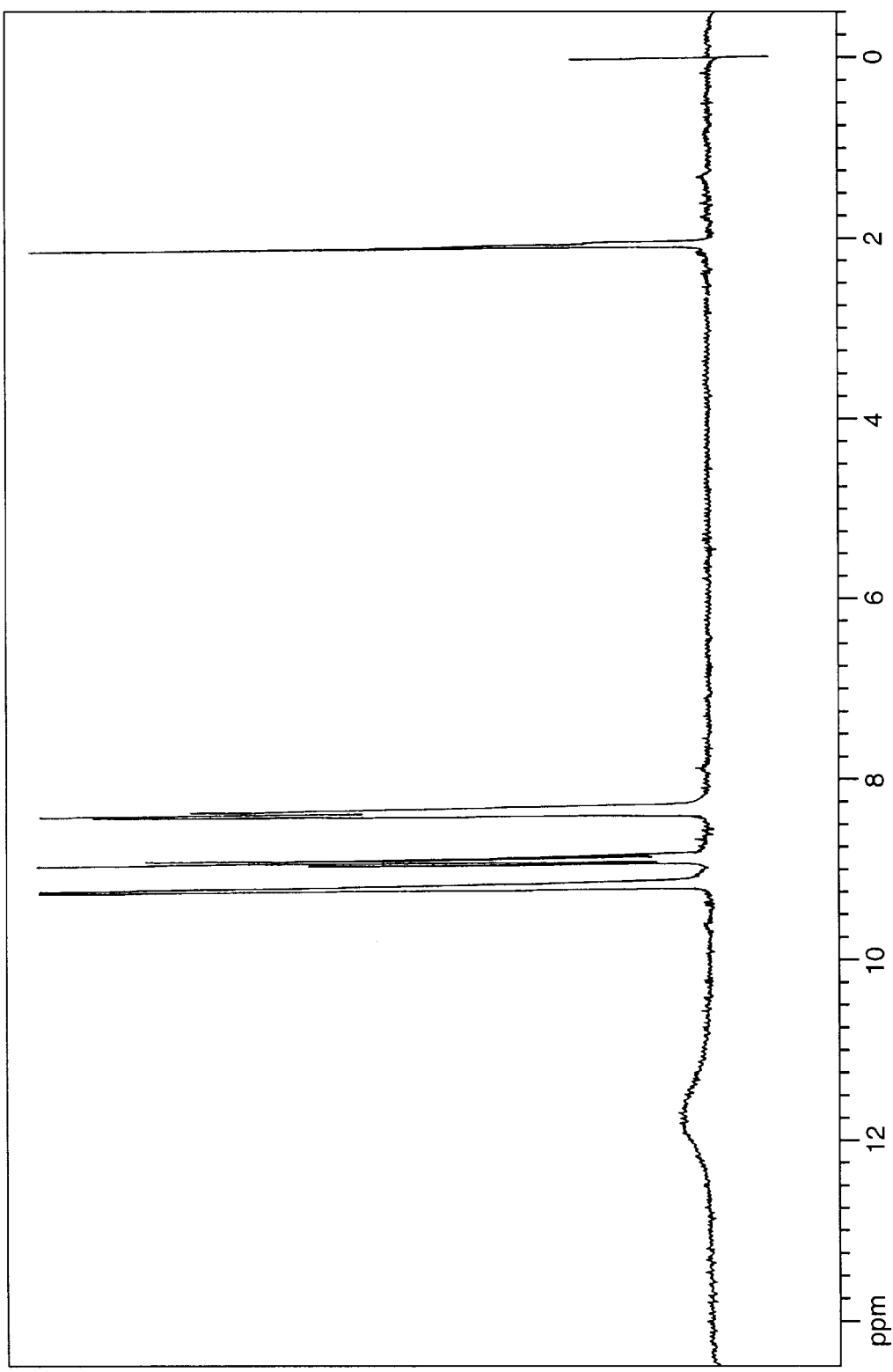
FIG._4

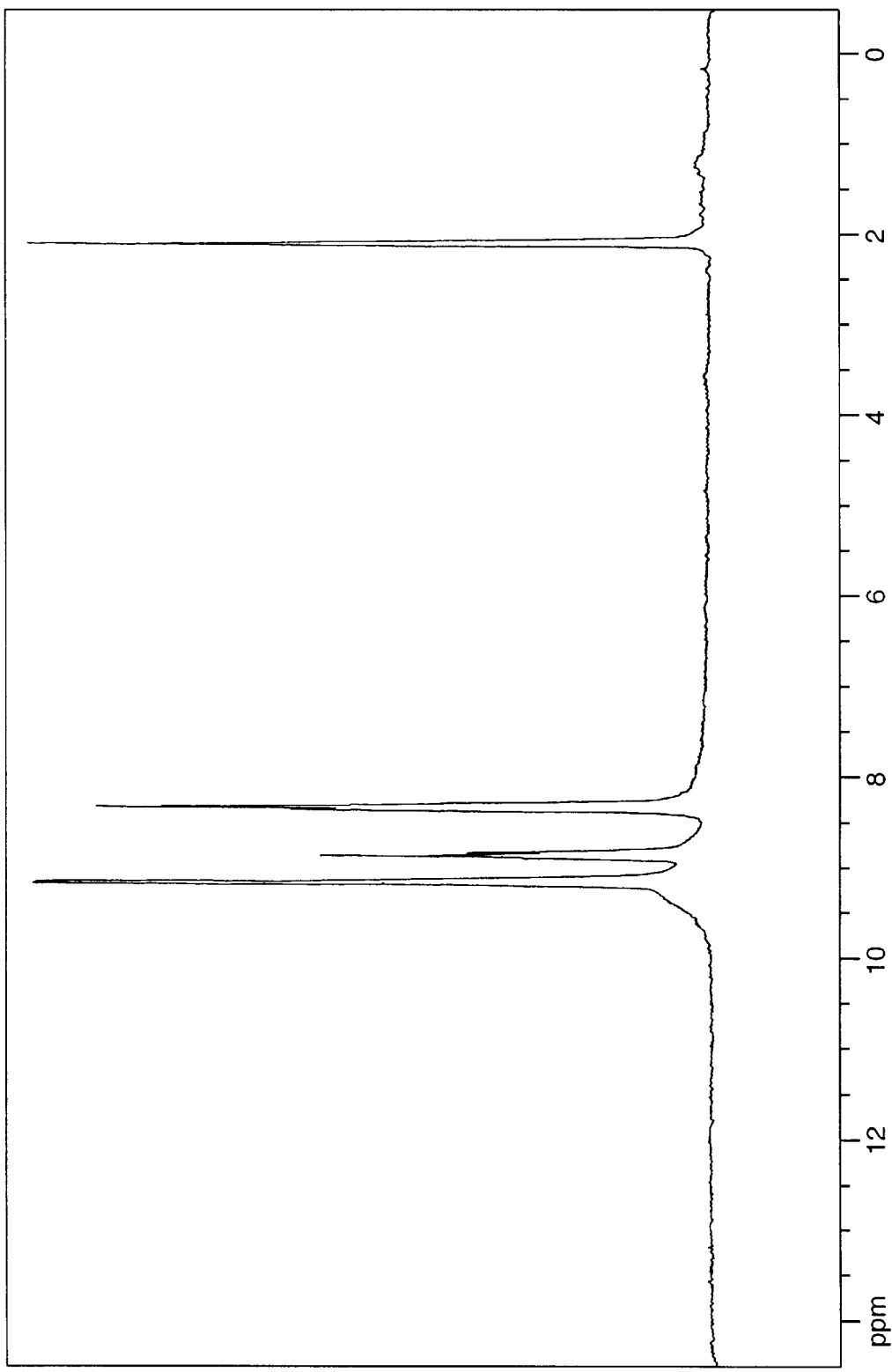
FIG._5

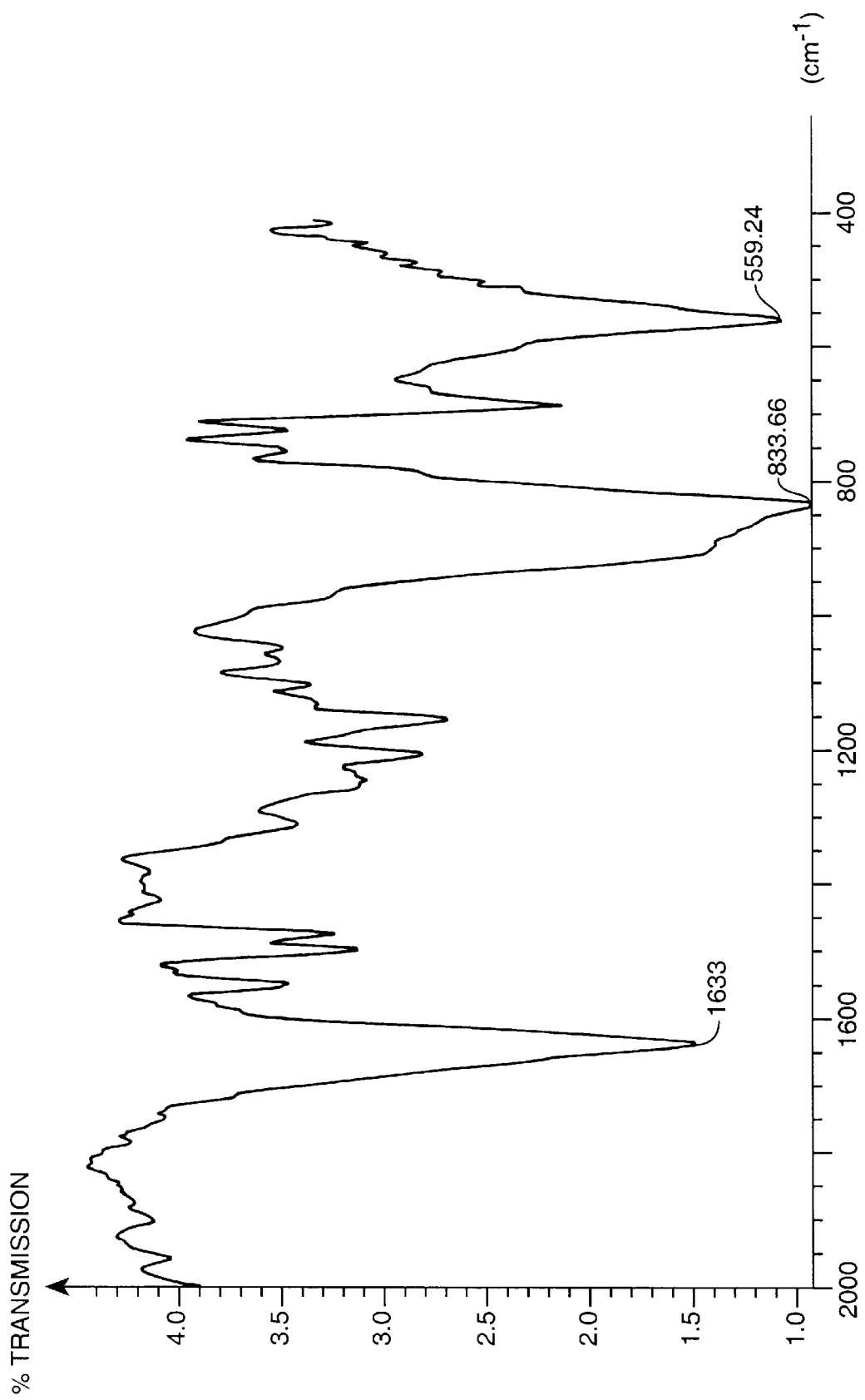
FIG._6

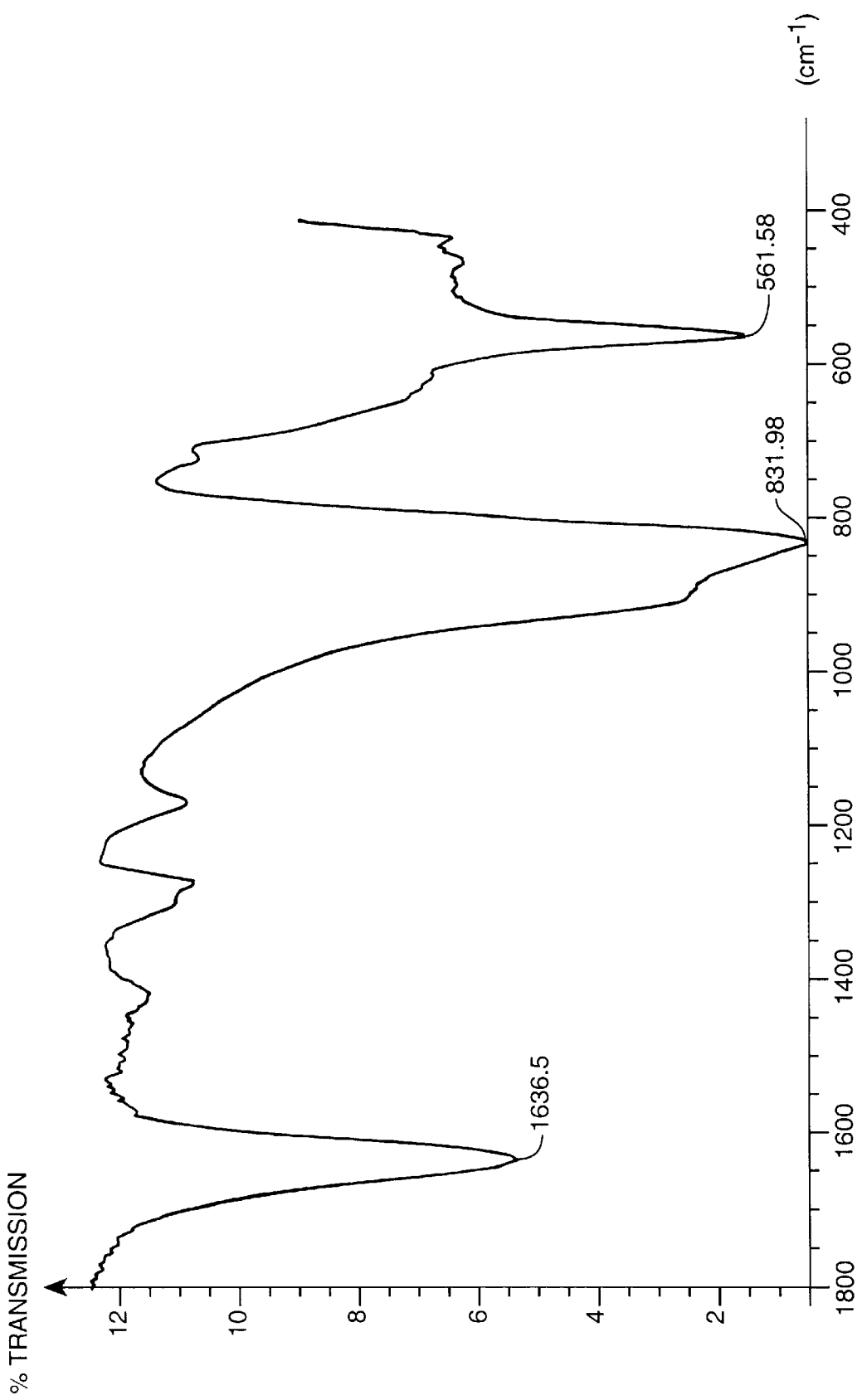
FIG._7

SOLVATE OF LITHIUM HEXAFLUOROPHOSPHATE AND PYRIDINE, ITS PREPARATION AND PREPARATION PROCESS FOR LITHIUM HEXAFLUOROPHOSPHATE USING SAID SOLVATE

DESCRIPTION

1. Technical Field

The invention relates to a novel compound constituted by a solvate of lithium hexafluorophosphate and pyridine usable for the preparation of lithium hexafluorophosphate.

It more particularly applies to the preparation of lithium hexafluorophosphate used as an electrolyte in lithium-carbon batteries.

At present lithium batteries are being extensively developed for various applications, particularly in electric vehicles, portable equipments such as portable telephones and camescopes, as well as in space. These batteries use an electrolyte constituted by one or more organic solvents containing in solution a lithium salt. Among the usable lithium salts, lithium hexafluorophosphate ($LiPF_6$) is at present the most widely used, due to its high solubility in organic solvents, its conductivity and its safety.

2. Prior Art

The conventional method for the preparation of $LiPF_6$ consists of reacting $PF_5$ with LiF in anhydrous hydrofluoric acid, but the purity of $LiPF_6$ prepared in this way is only 90 to 95%, whereas purities of at least 99% are required for use in a lithium battery in order to satisfy the $LiPF_6$ storage stability and solubility requirements.

In order to overcome this difficulty, it is still possible to obtain $LiPF_6$ of higher purity by the process described in U.S. Pat. No. 3,654,330. According to this process, lithium fluoride, anhydrous hydrofluoric acid and phosphorus pentafluoride $PF_5$ are reacted to obtain impure $LiPF_6$, which is then purified by reaction with acetonitrile. Thus, tetraacetonitrilolithium hexafluorophosphate $Li(CH_3CN)_4PF_6$ is produced, which then regenerates lithium hexafluorophosphate by heating in a partial vacuum. It is also possible to directly produce $Li(CH_3CN)_4PF_6$ by reacting $PF_5$ in a suspension of LiF in acetonitrile.

This process makes it possible to obtain high purity lithium hexafluorophosphate, but it suffers from the disadvantage of requiring the use of PF which is a very difficult product.

Another way for obtaining alkali metal hexafluorophosphates has been investigated by Syed Mohamed et al in J. Fluorine Chem., 23, 1983, pp 509–514. According to this document, the starting product is pyridinium hexafluorophosphate $C_5H_5NHPF_6$, which is then treated with an ammonium or alkali metal hydroxide in an aqueous medium, but this process has not made it possible to isolate solid $LiPF_6$ from said medium. Moreover, the preparation of the starting product $C_5H_5NHPF_6$ involves a low temperature reaction (−80° C.) between the pyridine and the anhydrous hydrofluoric acid, followed by the reaction of the product obtained with phosphoryl chloride. This involves difficult performance using expensive reagents ($POCL_3$), which is difficult to carry out on an industrial scale.

Lange et al in BER. 63B, 1058–70, 1930 describe the preparation of $C_5H_5NHPF_6$ by reacting pyridine in acetic acid with ammonium hexafluorophosphate. However, they did not envisage using this pyridinium hexafluorophosphate for preparing lithium hexafluorophosphate.

Thus, none of the presently known processes makes it possible to prepare high purity lithium hexafluorophosphate $LiPF_6$ under easily implementable conditions and without using onerous reagents.

DESCRIPTION OF THE INVENTION

The present invention relates to the preparation of high purity $LiPF_6$ by a simple, uncomplicated process using inexpensive, commercial products, with as the intermediate a solvate of lithium hexafluorophosphate and pyridine. It also relates to the solvate and its preparation process.

The solvate complies with the formula:

$$Li(C_5H_5N)PF_6$$

and has the advantage of being much easier to handle than $LiPF_6$, because it is stable in air at ambient temperature, whereas $LiPF_6$ decomposes into $PF_5$ and LiF and must be manipulated in a glove box. It also makes it possible to generate $LiPF_6$ with a high purity level of 99.8% using simple processes.

According to the invention, this solvate can be prepared by a process comprising the following stages:

a) preparation of pyridinium hexafluorophosphate of formula $C_5H_5NHPF_6$ by neutralization of hexafluorophosphoric acid $HPF_6$ with pyridine using the stoichiometric quantity permitting the neutralization of only the $HPF_6$ and not the other acid impurities present in the starting acid and b) conversion of pyridinium hexafluorophosphate into solvate $LiPF_6$, $C_5H_5N$ by exchange with a lithium compound chosen from among lithium hydroxide, lithium alkoxides and alkyl-lithiums.

In this process, the first stage a) is easy to perform, because it can be carried out in an aqueous medium at ambient temperature from an inexpensive, commercial product ($HPF_6$ in aqueous solution). Moreover, through using the precise stoichiometric quantity corresponding to the neutralization of $HPF_6$ and excluding other acid impurities present in the starting product, it is possible to obtain high purity pyridinium hexafluorophosphate, which will then lead to a high purity solvate $Li(C_5H_5N)PF_6$.

This stoichiometric quantity can be easily determined by carrying out before hand a neutralization test on the commercial acid $HPF_6$ used as the starting product and monitoring the neutralization by conductometry.

It has in fact been found that $HPF_6$ is stronger than the other acids present as impurities in commercial solutions and is neutralized first giving rise to a rapid conductivity drop of the solution. The end of this drop corresponds to the complete neutralization of $HPF_6$ and it is thus possible to determine the basic stoichiometric quantity necessary for this neutralization.

This method for preparing $C_5H_5NHPF_6$ is much easier to implement than that described by Syed Mohamed in J. Fluorine Chem., 23, 1983, pp 509–514, where said pyridinium hexafluorophosphate is obtained by a two-stage reaction, firstly preparing a poly(hydrogen fluoride)-pyridinium reagent at a temperature of −80° C., followed by the reaction of said reagent with dropwise added phosphoryl chloride.

The first stage of the process according to the invention is easier to perform, because it is carried out in an aqueous solution at ambient temperature. It also makes use of uncomplicated reagents, which are commercially available, such as $HPF_6$ solutions in water.

In the second stage b) of the process according to the invention, the pyridinium hexafluorophosphate is converted into solvate $Li(C_5H_5N)PF_6$ by exchange with a lithium compound. This solvate has the major advantage of being, unlike $LiPF_6$, stable at ambient temperature, permitting easier handling and storage.

According to a first embodiment of said stage, the lithium compound used is hydrated or unhydrated lithium hydroxide, in an alcoholic medium, e.g. methanol or ethanol. This reaction is fast and the solvate is obtained in solution in alcohol. It can then be obtained in solid form by evaporating the alcohol.

According to a second embodiment of conversion stage b), the lithium compound used is a lithium alkoxide and the exchange reaction takes place in the alcohol corresponding to lithium alkoxide.

In this case, it is possible to directly prepare the alkoxide in an alcoholic medium by dissolving lithium in an alcohol excess.

This reaction can also be performed in an aprotic medium, e.g. in tetrahydrofuran, other ethers or acetonitrile. This gives the solvent, as previously, by evaporation of the reaction medium constituted by the alcohol or aprotic solvent.

According to a third embodiment of stage b), the lithium compound used is an alkyl-lithium and the exchange reaction takes place in a saturated aliphatic hydrocarbon, such as hexane or pentane. The alkyl-lithiums which can be used are n-butyl lithium and tert. butyl lithium. In this case, the solvate precipitates in the reaction medium and can be recovered by filtration.

The invention also relates to a process for the preparation of lithium hexafluorophosphate from the solvate of lithium hexafluorophosphate and pyridine of formula:

$$Li(C_5H_5N)PF_6$$

According to this process, said solvate undergoes a vacuum decomposition at a temperature equal to or below 50° C. in order to eliminate the pyridine by volatilization.

This decomposition can be performed under dynamic vacuum, under a pressure below 1 Pa, at a temperature equal to or below 50° C. in order to avoid $LiPF_6$ decomposition.

According to a performance variant of this process, the solvate is reacted with concentrated sulphuric acid in order to eliminate the pyridine by precipitation in the form of pyridinium sulphate.

In order to carry out this reaction, the solvate is dissolved in an aprotic solvent, in which the pyridinium sulphate is insoluble, whereas the $LiPF_6$ is soluble therein. However, it is necessary to avoid the addition of a $H_2SO_4$ excess in order to avoid a lithium sulphate coprecipitation. The aprotic solvent can be tetrahydrofuran.

The solvate used as the starting product is advantageously prepared by the processes described hereinbefore.

This lithium hexafluorophosphate preparation procedure is particularly interesting, because the starting product, the solvate of $Li(C_5H_5N)PF_6$, can be prepared with a high degree of purity. Thus, from said solvate is obtained very pure lithium hexafluorophosphate using easily performable processes. In addition, the preparation of, the solvate by the processes described hereinbefore is easy to implement. Thus, it is possible to obtain high purity $LiPF_6$ at a cost lower than existing $LiPF_6$.

Finally, in view of the fact that the solvate is stable at ambient temperature the $LiPF_6$ handling and storage problems are obviated, because it can be regenerated from the solvate only, when this is necessary for preparing $LiPF_6$-based electrolyte.

Other features and advantages of the invention can be gathered from reading the following description given in an illustrative and non-limitative manner, with reference to the attached drawings.

BRIEF DESCRIPTION OF THE DRAWINGS

FIG. 1 is a graph illustrating the conductometric dosage curve of commercial hexafluorophosphoric acid by lithium hydroxide.

FIG. 2 shows the infrared spectrum of pyridinium hexafluorophosphate.

FIG. 3 shows the Raman spectrum of pyridinium hexafluorophosphate.

FIG. 4 illustrates the NMR spectrum of the pyridinium hexafluorophosphate proton.

FIG. 5 shows the NMR spectrum of the proton of the solvate $Li(C_5H_5N)PF_6$.

FIG. 6 shows the infrared spectrum of lithium hexafluorophosphate obtained by the process of the invention.

FIG. 7, for comparison purposes, shows the infrared spectrum of the commercial lithium hexafluorophosphate.

DETAILED DESCRIPTION OF EMBODIMENTS

The following examples illustrate the preparation of lithium hexafluorophosphate by the processes according to the invention.

EXAMPLE 1

Preparation of Pyridinium Hexafluorophosphate ($C_5H_5NHPF_6$)

In this example, the starting product is commercial, aqueous solution of hexafluorophosphoric acid $HPF_6$, which is a mixture of the strong acid $HPF_6$ and weak acids.

Firstly a determination takes place of the stoichiometric quantity necessary for solely converting the strong acid $HPF_6$ of said commercial solution into pyridinium hexafluorophosphate. This is brought about by neutralizing said solution, which contains 0.196 g of $HPF_6$ for 20 cm³ of water, by 0.98 N lithium hydroxide and following or monitoring the neutralization by conductometry.

FIG. 1 shows the curve obtained under these conditions, namely the evolution of the conductivity (in mS. cm$^{-1}$) of the solution, as a function of the added lithium hydroxide volume (in cm³).

It can be seen that the first section of the conductometry curve is linear and corresponds up to the volume $V_1$ to the neutralization of $HPF_6$. As from $V_1$ and up to the volume $V_2$, the lithium hydroxide addition does not modify the conductivity of the solution. This corresponds to the neutralization of the weaker acid impurities. Beyond $V_2$, the conductivity of the solution increases linearly, because the neutralization of the acids is ended.

This determines the basic quantity corresponding to the volume $V_1$ making it possible to neutralize solely the strong acid $HPF_6$. This quantity corresponds to 10.5 cm³ of 0.098 N lithium hydroxide for 20 cm³ of commercial aqueous solution containing 0.196 g of $HPF_6$. On the basis of these results, pyridinium hexafluorophosphate is prepared using the same commercial hexafluorophosphoric acid batch and working in the following way.

Dropwise addition takes place of 7.2 cm³ of pyridine to 20 g of aqueous commercial $HPF_6$ solution (Fluka product having a 65% $HPF_6$ content) placed in ice. Pyridinium hexafluorophosphate precipitation is immediate and the latter is separated by filtration. This is followed by three recrystallizations in water and then one in absolute methanol, followed finally by one in absolute ethanol. This gives 11.3 g of pyridinium hexafluorophosphate, which corresponds to a total yield of 49%. The product is then treated in the oven at 110° C. up to constant weight.

FIG. 2 shows the infrared spectrum of the product obtained. It is possible to see the two characteristic bands of $PF_6^-$ at 557.71 (558) and 832.35 (832) with a shoulder at 890 cm$^{-1}$. The other bands are attributed to the pyridinium nucleus, including that at 1642 cm$^{-1}$, which can be confused with that between 1630 and 1645 cm$^{-1}$, which occurs in all the IR spectra of $LIPF_6$ and which is without doubt a harmonic of the band at 832 cm$^{-1}$.

Thus, the infrared spectrum of the product has bands identical to those described by Syed Mohamed et al in J. Fluorine Chem., 23, 1983, pp 509–514 and in Spectrochimica Acta, 41A(5), 1985, pp 725–728.

FIG. 3 shows the Raman spectrum of the product obtained and it is possible to see thereon the band at 1008.6 cm$^{-1}$, which corresponds to N—H$^+$.

FIG. 4 shows the NMR spectrum of the proton. On this spectrum the widened singlet at 11.68 ppm (11.7 ppm) corresponds to N—H$^+$.

The percentage analysis of the product obtained is given in the following table 1:

TABLE 1

|  | C% | N% | F% | P% |
| --- | --- | --- | --- | --- |
| Obtained | 26.67 | 6.11 | 45.90 | 13.50 |
| Calculated | 26.68 | 6.22 | 50.64 | 13.76 |

The purity check carried out in accordance with the principle adopted by Syed Mohamed et al using lithium hydroxide in place of soda revealed that the salt had a degree of purity of 99.8%.

It is possible to improve by at least 20% the $C_5H_5NHPF_6$ yield of this example by performing only one recrystallization in water and one in absolute methanol, because the infrared spectrum of the product obtained is the same as that obtained after all the aforementioned recrystallizations.

EXAMPLE 2

Preparation of the Solvate $LiPF_6$, Pyridine

In this example, the pyridinium hexafluorophosphate obtained in example 1, is transformed into solvate $LiPF_6$, pyridine, by reaction with lithium hydroxide in an absolute ethanol medium.

To this end, 0.42 g (10$^{-2}$ mole) of commercial lithium hydroxide (LiOH, H$_2$O) is added to 2.25 g (10$^{-2}$ mole) of pyridinium hexafluorophosphate $C_5H_5NHPF_6$ obtained in example 1, suspended in 50 cm$^3$ of absolute ethanol, in which the salt is only slightly soluble. The reaction is fast and solubilization complete. This is followed by the addition of 20 cm$^3$ of anhydrous benzene, so as to eliminate under partial vacuum the ternary benzene-ethanol-water azeotrope. This gives 2.1 g of solid product, which is the solvate $LiPF_6$, pyridine, which corresponds to a 91% yield.

The infrared and Raman spectra of this product $LiPF_6 C_5H_5N$ are identical to those of the $C_5H_5NHPF_6$ obtained in example 1. Thus, N—H$^+$ and N—Li both give the band at approximately 1008 cm$^{-1}$ in Raman spectrometry and only the pyridines solvated by H$_2$O are towards 1026 cm$^{-1}$. In infrared, the NH band passes to 3300 cm$^{-1}$, which belongs to an unusable range of the spectrum.

FIG. 5 shows the NMR spectrum of the proton of this solvate. It is possible to see that the singlet at 11.68 ppm is absent, whereas it would appear on the spectrum of FIG. 4 corresponding to the product $C_5H_5NHPF_6$ of example 2.

The percentage analysis of the solvate is given in the following table 2.

TABLE 2

| | Percentage composition | | | |
| --- | --- | --- | --- | --- |
| Li(C$_5$H$_5$N)PF$_6$ | C% | F% | P% | Li% |
| Example 2 | 22.61 | 49.41 | 12.70 | 3.90 |
| Example 3 | 22.00 | 49.37 | 12.85 | 3.50 |
| Calculated | 26.00 | 49.34 | 13.41 | 3.00 |

EXAMPLE 3

Preparation of the Solvate $LiPF_6$, Pyridine

This example follows the operating procedure of example 2, but using absolute methanol as the reaction medium. In this case, 0.84 g of LIOH, H$_2$O in powder form is added to 4.5 g of $C_5H_5NHPF_6$ obtained in example 1 in 100 cm$^3$ of absolute methanol. As previously, the reaction is fast and solubilization complete. The methanol is then evaporated after adding 40 cm$^3$ anhydrous benzene and eliminating under a partial vacuum the benzene-methanol-water ternary azeotrope. This gives 2.9 g of solid product, which is the solvate $LiPF_6$, pyridine.

The characteristics of this product are identical to those of the product obtained in example 2. The percentage analysis is given in table 2.

In table 2, the values found for Li, higher than the calculated percentage, are explained by the fact that during the elimination of the alcohols under a partial vacuum, a fraction of the complex may have been destroyed in accordance with Li(C$_5$H$_5$N)PF$_6$→C$_5$H$_5$N (vacuum entrained)+ LiPF$_6$. A further consequence is a drop in its carbon percentage.

This result is compatible with the analysis of lithium by atomic absorption, because 2.33 and 2.48 ppm were found, respectively for examples 2 and 3, whereas the theoretical value would be 1.98 ppm for Li in the pure complex and 3.01 ppm for Li in LiPF$_6$.

EXAMPLE 4

Preparation of the Solvate $LiPF_6$, Pyridine

In this example the starting product is the pyridinium hexafluorophosphate obtained in example 1 and it is converted into solvate by exchange with a lithium alkoxide constituted by lithium methanolate.

The lithium methanolate is firstly prepared from a piece of metallic lithium placed in a bottle previously calibrated under dry argon. To this bottle are added 50 cm$^3$ of methanol for 2.2.10$^{-2}$ mole of lithium. As soon as the alkoxide has formed, the equivalent stoichiometric quantity of pyridinium hexafluorophosphate obtained in example 1 is suspended in the bottle. The reaction is fast, the final mixture being free from water. The solvate is obtained by evaporating the solvent without adding anhydrous benzene. After evaporation under partial vacuum at 30° C., the solvate $LiPF_6$, pyridine is obtained in a quasi-quantitative form.

EXAMPLE 5

Preparation of the Solvate $LiPF_6$, Pyridine

This example follows the operating procedure of example 4, but as the lithium alkoxide use is made of lithium ethanolate, which is prepared in the same way by adding ethanol to a bottle containing a piece of lithium. The solvate $LiPF_6$, pyridine is also obtained in a quasi-quantitative form.

EXAMPLE 6

Preparation of Solvate $LiPF_6$, Pyridine

In this example, the salt obtained in example 1 is converted into solvate using butyl-lithium as the lithium compound. $8.10^{-3}$ mole of $C_5H_5NHPF_6$ obtained in example 1 are suspended in 5 cm$^3$ of 1.6 M butyl-lithium solution in hexane (Aldrich solution) under argon. At ambient temperature, the reaction evolves in about 20 hours and a total solvate precipitation is obtained. The solvate is recovered by filtration and is then washed with $CH_2Cl_2$.

The solvate obtained has the same characteristics as that obtained in the previous examples.

EXAMPLE 7

Preparation of the Solvate $LiPF_6$, Pyridine

This example follows the same operating procedure as in example 6, but tert. butyl lithium is used as the lithium compound. In small portions $8.5\ 10^{-3}$ mole of $C_5H_5NHPF_6$ obtained in example 1 are added to 5 cm$^3$ of a 1.7 M. tert. butyl lithium solution in pentane (Aldrich solution) kept at $-20°$ C. The reaction is fast and highly exothermic, which leads to the boiling of the pentane. The product precipitates as in example 6 and it is recovered by filtration, followed by washing with $CH_2Cl_2$, as previously.

The characteristics of the product obtained are identical to those obtained with the preceding examples.

EXAMPLE 8

Preparation of the Solvate $LiPF_6$, Pyridine

In this example, the pyridinium salt obtained in example 1 is converted into solvate using lithium methanolate in an aprotic medium as the lithium compound. In this case, $1.26\ 10^{-2}$ mole of lithium are reacted with 20 cm$^3$ of absolute methanol to form lithium methanolate, as in example 4. After evaporating the methanol, the dry residue is suspended in 20 cm$^3$ of tetrahydrofuran (THF). Preparation also takes place of a suspension of the salt $C_5H_5NHPF_6$ obtained in example 1 suspending 2.85 g of said salt in 40 cm$^3$ of THF. The two suspensions are then mixed. The reaction is fast and there is a total solubilization of the solvate. The solvate is then isolated by eliminating THF by partial vacuum evaporation at ambient temperature. The product obtained has the same characteristics as that obtained in the preceding examples.

EXAMPLE 9

Preparation of $LiPF_6$

In this example, $LiPF_6$ is prepared by vacuum decomposition of the solvate obtained in example 2, working under a dynamic vacuum at a pressure below 1 Pa and a temperature of 50° C., pure $LiPF_6$ is directly obtained.

FIG. 6 shows the infrared spectrum of the product obtained under these conditions and which corresponds to $LiPF_6$. Thus, the bands are at $\upsilon(P\text{---}F)=832$ cm$^{-1}$ with a shoulder at 888 cm$^{-1}$ and $\delta(P\text{---}F)$ at 559 cm$^{-1}$.

The finally regenerated $LiPF_6$ purity, estimated by Li dosing in atomic absorption is close to 99% (98.7 and 98.9%).

FIG. 7 shows for comparison purposes the infrared spectrum of the commercial Aldrich product $LiPF_6$. This spectrum reveals the same bands at 832 (890) and 561 cm$^{-1}$.

EXAMPLE 10

Preparation of $LiPF_6$, Pyridine

In this example, $LiPF_6$ is prepared from the solvate $LiPF_6$, pyridine obtained in example 8 separating the pyridine by precipitation in pyridinium sulphate form. To this end, to the solution of the solvate in THF obtained in example 8 is added concentrated sulphuric acid (96%), which leads to the precipitation of the pyridinium sulphate. The solution is then filtered to eliminate the precipitate, followed by the vacuum evaporation of the organic solvent at a temperature below 50° C. Thus, $LiPF_6$ is very rapidly obtained.

We claim:

1. Solvate of lithium hexafluorophosphate and pyridine of formula:

$Li(C_5H_5N)PF_6$.

2. Process for the preparation of the solvate of lithium hexafluorophosphate and pyridine of formula:

$Li(C_5H_5N)PF_6$ characterized in that it comprises the following stages:
 a) preparation of pyridinium hexafluorophosphate of formula $C_5H_5NHPF_6$ by neutralization of hexafluorophosphoric acid $HPF_6$ with pyridine using the stoichiometric quantity permitting the neutralization of only the $HPF_6$ and not the other acid impurities present in the starting acid and
 b) conversion of the pyridinium hexafluorophosphate into solvate $Li(C_5H_5N)PF_6$ by exchange with a lithium compound selected from the group consisting of lithium hydroxide, lithium alkoxides and alkyl-lithiums.

3. Process according to claim 2, characterized in that in stage b) use is made of hydrated or unhydrated lithium hydroxide and the exchange reaction is performed in an alcoholic medium.

4. Process according to claim 3, characterized in that the alcohol is methanol or ethanol.

5. Process according to claim 2, characterized in that in stage b) use is made of a lithium alkoxide and the exchange reaction is performed in the alcohol corresponding to lithium alkoxide or in an aprotic medium.

6. Process according to claim 5, characterized in that the lithium alkoxide is lithium methanolate or ethanolate.

7. Process according to claim 6, characterized in that the aprotic medium is tetrahydrofuran.

8. Process according to claim 5, characterized in that the aprotic medium is tetrahydrofuran.

9. Process according to claim 2, characterized in that in stage b) use is made of an alkyl-lithium and the exchange reaction is performed in a saturated aliphatic hydrocarbon.

10. Process according to claim 9, characterized in that the alkyl-lithium is butyl lithium or tert. butyl lithium.

11. Process for the preparation of lithium hexafluorophosphate $LiPF_6$, characterized in that it consists of subjecting the solvate of lithium hexafluorophosphate and pyridine of formula:

$Li(C_5H_5N)PF_6$ to a vacuum decomposition at a temperature equal to or below 50° C. in order to eliminate the pyridine by volatilization.

12. Process according to claim 11, characterized in that the solvate is prepared by a process comprising the following stages:
   a) preparation of pyridinium hexafluorophosphate of formula $C_5H_5NHPF_6$ by neutralization of hexafluorophosphoric acid $HPF_6$ with pyridine using the stoichiometric quantity permitting the neutralization of only $HPF_6$ and not the other acid impurities present in the starting acid and
   b) conversion of the pyridinium hexafluorophosphate into solvate $Li(C_5H_5N)PF_6$ by exchange with a lithium compound selected from the group consisting of lithium hydroxide, lithium alkoxides and alkyllithiums.

13. Process for the preparation of lithium hexafluorophosphate $LiPF_6$, characterized in that the solvate of lithium hexafluoride and pyridine of formula $Li(C_5H_5N)PF_6$ is reacted with sulphuric acid to eliminate the pyridine by precipitation in the form of pyridinium sulphate.

14. Process according to claim 13, characterized in that the solvate is prepared by a process comprising the following stages:
   a) preparation of pyridinium hexafluorophosphate of formula $C_5H_5NHPF_6$ by neutralization of hexafluorophosphoric acid $HPF_6$ with pyridine using the stoichiometric quantity permitting the neutralization of only $HPF_6$ and not the other acid impurities present in the starting acid and
   b) conversion of the pyridinium hexafluorophosphate into solvate $Li(C_5H_5N)PF_6$ by exchange with a lithium compound selected from the group consisting of lithium hydroxide, lithium alkoxides and alkyllithiums.

* * * * *